(12) United States Patent
Salnik et al.

(10) Patent No.: US 7,502,104 B2
(45) Date of Patent: Mar. 10, 2009

(54) PROBE BEAM PROFILE MODULATED OPTICAL REFLECTANCE SYSTEM AND METHODS

(75) Inventors: Alex Salnik, Castro Valley, CA (US); Lena Nicolaides, Castro Valley, CA (US); Jon Opsal, Livermore, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 11/890,712

(22) Filed: Aug. 6, 2007

(65) Prior Publication Data

US 2008/0036998 A1 Feb. 14, 2008

Related U.S. Application Data

(60) Provisional application No. 60/836,763, filed on Aug. 10, 2006.

(51) Int. Cl.
*G01N 21/00* (2006.01)

(52) U.S. Cl. .................... 356/237.2; 356/237.5
(58) Field of Classification Search .................. None
See application file for complete search history.

(56) References Cited

U.S. PATENT DOCUMENTS

| | | | | |
|---|---|---|---|---|
| 4,634,290 A | | 1/1987 | Rosencwaig et al. | 374/5 |
| 4,636,088 A | | 1/1987 | Rosencwaig et al. | 374/5 |
| 4,679,946 A | | 7/1987 | Rosencwaig et al. | 374/5 |
| 4,795,260 A | * | 1/1989 | Schuur et al. | 356/400 |
| 4,854,710 A | | 8/1989 | Opsal et al. | 356/432 |
| 4,870,263 A | | 9/1989 | Deutsch | 250/201 |
| 4,999,014 A | | 3/1991 | Gold et al. | 356/382 |
| 5,042,951 A | | 8/1991 | Gold et al. | 356/369 |
| 5,074,669 A | * | 12/1991 | Opsal | 356/445 |
| 5,142,473 A | | 8/1992 | Davis | 701/21 |
| 5,166,752 A | | 11/1992 | Spanier | 356/369 |
| 5,181,080 A | | 1/1993 | Fanton et al. | 356/381 |
| 5,412,473 A | | 5/1995 | Rosencwaig et al. | 356/351 |
| 5,596,411 A | | 1/1997 | Fanton et al. | 356/369 |
| 5,608,526 A | | 3/1997 | Piwonka-Corle et al. | 356/369 |
| 5,798,837 A | | 8/1998 | Aspnes et al. | 356/369 |
| 5,880,845 A | | 3/1999 | Leroux | 356/376 |
| 5,889,593 A | | 3/1999 | Bareket | 356/445 |
| 5,978,074 A | | 11/1999 | Opsal et al. | 356/72 |
| 6,151,522 A | * | 11/2000 | Alfano et al. | 600/473 |
| 6,268,916 B1 | | 7/2001 | Lee et al. | 356/369 |
| 6,429,943 B1 | | 8/2002 | Opsal et al. | 356/625 |
| 6,678,046 B2 | | 1/2004 | Opsal | 356/369 |
| 6,784,993 B2 | * | 8/2004 | Opsal et al. | 356/369 |
| 6,813,034 B2 | | 11/2004 | Rosencwaig et al. | 356/601 |

(Continued)

FOREIGN PATENT DOCUMENTS

EP 1 640 706 A1 3/2006

*Primary Examiner*—Michael P Stafira
(74) *Attorney, Agent, or Firm*—Stallman & Pollock LLP

(57) ABSTRACT

The present invention provides a probe beam profile—modulated optical reflectivity metrology system having a modulated pump source for exciting the sample. A separate probe beam is directed to interact with the sample in a manner so that the rays within the probe beam create a spread of angles of incidence. A detector array simultaneously measures intensities of the rays within the reflected/diffracted probe beam simultaneously at different angles of incidence. The intensity and angle of incidence information is used to analyze the sample.

24 Claims, 1 Drawing Sheet

U.S. PATENT DOCUMENTS

| | | | |
|---|---|---|---|
| 6,888,632 B2 | 5/2005 | Smith | 356/369 |
| 6,952,261 B2 | 10/2005 | Ebert | 356/369 |
| 6,989,899 B2 | 1/2006 | Salnik et al. | 356/432 |
| 7,106,446 B2 | 9/2006 | Nicolaides et al. | 356/445 |
| 7,126,690 B2 | 10/2006 | Opsal et al. | 356/445 |
| 7,206,070 B2 | 4/2007 | Opsal | 356/369 |
| 7,212,288 B2 | 5/2007 | Opsal et al. | 356/432 |
| 7,248,367 B2 | 7/2007 | Salnik et al. | 356/432 |
| 2003/0234933 A1* | 12/2003 | Nicolaides et al. | 356/445 |
| 2004/0196453 A1* | 10/2004 | Some | 356/237.1 |
| 2004/0239933 A1* | 12/2004 | Opsal et al. | 356/369 |
| 2004/0253751 A1 | 12/2004 | Salnik et al. | 438/16 |
| 2005/0062971 A1 | 3/2005 | Salnik et al. | 356/432 |
| 2005/0140976 A1* | 6/2005 | Hovinen et al. | 356/369 |
| 2005/0195399 A1 | 9/2005 | Nicolaides et al. | 356/432 |
| 2006/0098198 A1* | 5/2006 | Chism, II | 356/369 |
| 2006/0166385 A1 | 7/2006 | Salnik et al. | 438/17 |
| 2007/0188762 A1* | 8/2007 | Smith | 356/432 |

* cited by examiner

PROBE BEAM PROFILE MODULATED OPTICAL REFLECTANCE SYSTEM AND METHODS

PRIORITY DATA

This application claims priority to U.S. Provisional Application Ser. No. 60/836,763, filed Aug. 10, 2006, the disclosure of which is incorporated herein by reference.

TECHNICAL FIELD

The subject invention relates to an optical metrology device used to non-destructively evaluate semiconductor wafers. In particular, the present invention relates to systems for characterizing the process of ion implantation and monitoring the parameters of ultra-shallow junctions formed in semiconductor samples.

BACKGROUND OF THE INVENTION

As geometries continue to shrink, manufacturers have increasingly turned to optical techniques to perform non-destructive inspection and analysis of semiconductor wafers. The basis for these techniques is the notion that a sample may be examined by analyzing the reflected energy that results when an optical beam is directed at a sample. This type of inspection and analysis is known as optical metrology and is performed using a range of different optical techniques.

One widely used type of optical metrology system includes a pump laser. The pump laser is switched on and off to create an intensity-modulated pump beam. The pump beam is projected against the surface of a sample causing localized heating of the sample. As the pump laser is modulated, the localized heating (and subsequent cooling) creates a train of thermal and plasma waves within the sample. These waves reflect and scatter off various features and interact with various regions within the sample in a way that alters the flow of heat and/or plasma from the pump beam spot.

The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

To monitor the surface changes, a probe beam is directed at a portion of the sample that is illuminated by the pump laser. A photodetector records the intensity of the reflected probe beam. The output signal from the photodetector is filtered to isolate the changes that are synchronous with the pump beam modulation. For most implementations, this is performed using a heterodyne or lock-in detector (See U.S. Pat. No. 5,978,074 and, in particular, FIG. 2 for a discussion of such a lock-in amplifier/detector). Devices of this type typically generate separate "in-phase" (I) and "quadrature" (Q) outputs. These outputs are then used to calculate amplitude and phase of the modulated signal using the following equations:

$$\text{Amplitude} = \sqrt{I^2 + Q^2} \quad (1)$$

$$\text{Phase} = \arctan(Q/I) \quad (2)$$

The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for test samples can then be analyzed by comparison to the amplitude values obtained for the calibration samples.

Systems of this type (i.e., those using external means to induce thermal or plasma waves in the sample under study) are generally referred to as MOR (modulated optical reflectance) type systems. MOR-type systems are used to study a range of attributes, including material composition and layer thickness. MOR-type systems and their associated uses are described in more detail in U.S. Pat. Nos. 4,634,290, 4,636,088, 4,679,946; 4,854,710, 5,978,074 and 5,074,669. Each of these patents is incorporated in this document by reference. The assignee manufactures a commercial device, the Therma-Probe which operates using the MOR technique.

An important use of MOR-type systems is the measurement and analysis of the dopants added to semiconductor wafers before and after their activation. Dopants are ions that are implanted to semiconductors during a process known as ion implantation. The duration of the ion implantation process (i.e., total exposure of the semiconductor wafer) controls the resulting dopant concentration. The ion energy used during the implantation process controls the depth of implant. Both concentration and depth are critical factors that determine the overall effectiveness of the ion implantation process.

MOR-type systems are typically used to inspect wafers at the completion of the ion implantation process. The ion implantation damages the crystal lattice as incoming ions come to rest. This damage is typically proportional to the concentration and depth of ions within the crystal lattice. This makes measurement of damage an effective surrogate for direct measurement of dopant concentration and depth.

In one approach, an MOR-type optical metrology tool with an advanced signal processing algorithm is used to record both quadrature (Q) and in-phase (I) components of the signal for a series of specially prepared calibration samples. The measurement method then performs a linear fit using the recorded points to define a calibration line within an I-Q plane. The slope of this line is defined by the implantation energy and the points along the line correspond to different dopant concentrations. Thus, the damage profile can be characterized by comparison of measured and calibration data in I-Q space. Characterization of samples using I and Q outputs is described in U.S. Pat. No. 6,989,899, assigned to the same assignee and incorporated here by reference.

Dopant activation after the ion implantation step is usually performed by rapidly heating and cooling the sample is a special chamber. This process is also known as annealing of semiconductor wafers. During the anneal, dopant ions diffuse away from the surface and form a concentration profile within the sample. The transition between the implanted region containing activated dopants and the non-implanted substrate is commonly referred to as a junction. For advanced semiconductor manufacturing, it is generally desirable for the implanted and activated region to be shallow, typically 500 Å or less. Devices of this type are generally referred to as having ultra-shallow junctions or USJ.

A number of techniques have been developed to characterize the effectiveness of USJ process. Destructive and contact methods include secondary ion mass spectroscopy (SIMS), transmission electron microscopy (TEM), and spreading resistance depth profiling (SRP). These techniques are capable of providing detailed USJ profile information, but at the expense of a turnaround time that is usually measured in days or even weeks or at the expense of damaging the surface with contacts.

Alternately, U.S. Pat. No. 7,248,367, assigned to the same assignee and incorporated here by reference, describes a non-destructive MOR-type system for simultaneous measurements of junction depth ($X_j$) and abruptness. System of this type performs a series of measurements at different separations between the pump and probe beams followed by the analysis of measured data in I-Q space. Similar approach to measure USJ depth and abruptness is described in the following publications: L. Nicolaides et al., Rev. Sci. Instrum. 74(1), 586 (2003) and A. Salnik et al., Rev. Sci. Instrum. 75(6), 2144 (2004) incorporated here by reference.

The assignee of the subject invention has previously developed simultaneous multiple angles of incidence measurement tools which have been used to derive characteristics of thin films of semiconductor wafers and to obtain critical dimension measurements on grating structures. Detailed description of assignee's simultaneous multiple AOI devices can be found in the following U.S. Pat. Nos. 4,999,014; 5,042,951; 5,181,080; 5,142,473 and 5,596,411, all incorporated herein by reference. The assignee manufactures a commercial device, the Opti-Probe which takes advantage of some of these simultaneous multiple angles of incidence systems.

One of these simultaneous multiple angles of incidence tools is marketed by the assignee under the name Beam Profile Reflectometer (BPR). In this tool, a probe beam is focused with a strong lens so that the rays within the probe beam strike the sample at multiple angles of incidence. The reflected beam is directed to an array photodetector. The intensity of the reflected beam as a function of radial position within the beam is measured and includes not only the specularly reflected light but also the light that has been scattered into that detection angle from all the incident angles as well. Thus, the radial positions of the rays in the beam illuminating the detector correspond to different AOI on the sample plus the integrated scattering from all of the angles of incidence contained in the incident beam. In this manner, simultaneous multiple angles of incidence reflectometry can be performed.

Another tool used by the assignee is known as Beam Profile Ellipsometry (BPE). In one embodiment as shown and described in U.S. Pat. No. 5,042,951, the arrangement is similar to that described for BPR technology except that additional polarizers and/or analyzers are provided. In this arrangement, the change in polarization state of the various rays within the probe beam is monitored as a function of angle of incidence.

It is believed that the BPR/BPE technologies can be combined with the MOR measurement system to provide more information about the semiconductor sample under investigation.

SUMMARY OF THE INVENTION

The present invention provides a probe beam profile MOR (PBP-MOR) metrology system having a modulated pump source for exciting the sample. A separate probe beam is directed to interact with the sample in a manner so that the rays within the probe beam create a spread of angles of incidence. A detector array simultaneously measures modulated intensities of the rays within the reflected/diffracted probe beam simultaneously at different angles of incidence. The modulated intensity and angle of incidence information is used to analyze the sample.

DETAILED DESCRIPTION OF THE PREFERRED EMBODIMENT

Figure 1:
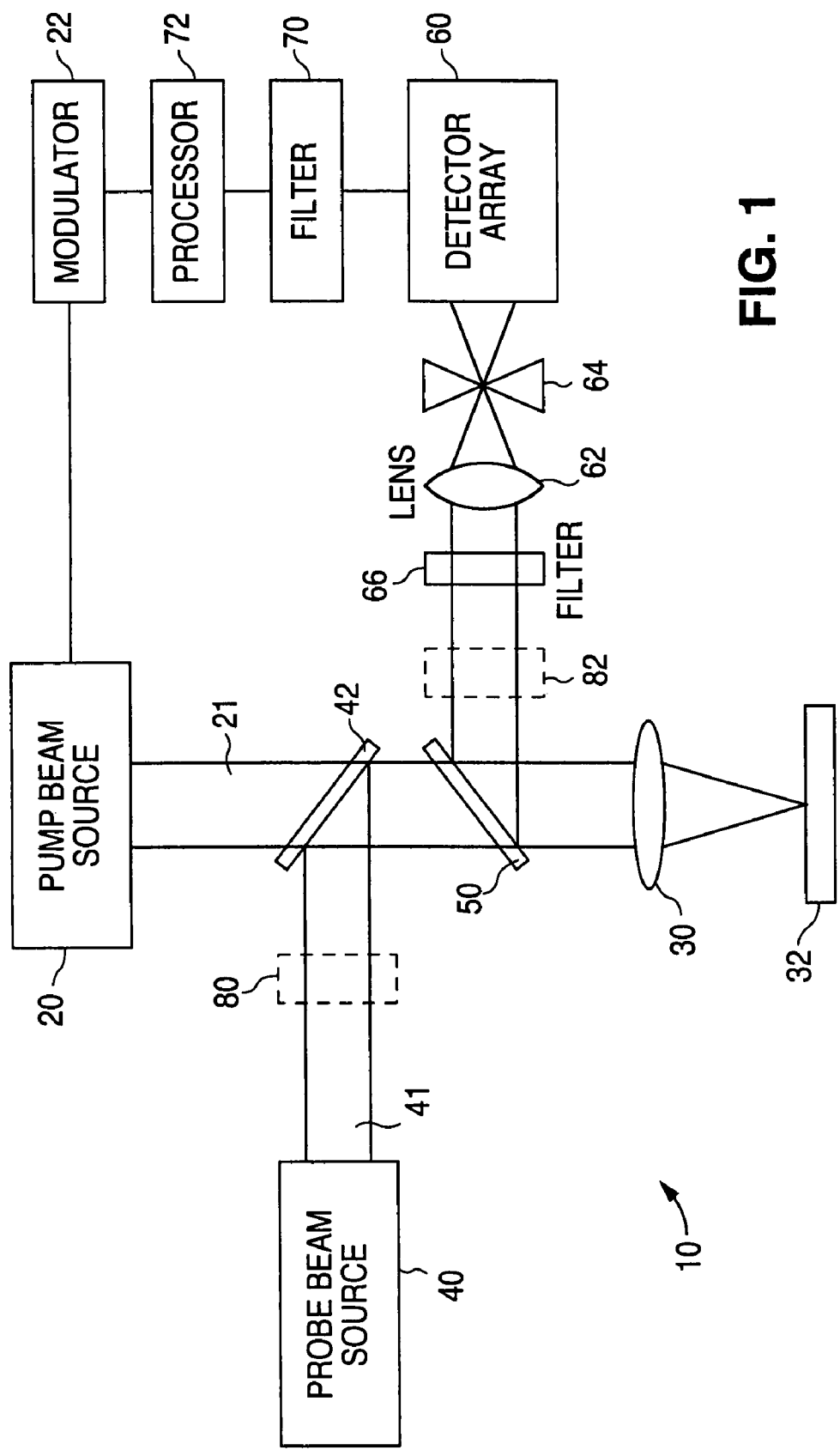
FIG. 1 is a schematic diagram of a preferred embodiment of the subject invention.

A schematic diagram of the PBP-MOR system configured in accordance with the subject invention is shown in FIG. 1. The system 10 is intended to be used to perform evaluations of the type associated with prior MOR and BPR/BPE systems.

The subject PBP-MOR system includes a light source 20 for generating a pump beam of radiation 21. Pump beam source may be an intensity modulated laser or incoherent light source. Gas, solid state or semiconductor lasers can be used, including laser systems coupled with a fiber. The pump beam induces a modulation of the optical characteristics of the sample which may be due to the generation of the thermal and plasma waves affecting the optical properties of the sample. The pump beam is intensity modulated at a predetermined frequency, selected upon the desired experimental conditions. Other means for exciting the sample can include different sources of electromagnetic radiation or particle beams such as from an electron gun or pump beam position modulation as illustrated in U.S. Pat. No. 7,212,288 incorporated herein by reference. In the preferred embodiment of the latter patent, the pump beam is not intensity modulated but instead is dithered around a center point to create periodic localized excitation.

In a preferred embodiment, the pump source is a laser. The laser is intensity modulated by a drive signal supplied by a modulator 22. The modulation frequency can vary from a few hertz to tens of megahertz. In one preferred embodiment, the modulation frequency is on the order of one megahertz. This is a frequency which will create plasma waves in a typical semiconductor the sample.

A lens 30 can be used to focus the pump beam 21 onto the sample 32. The pump beam spot size on the sample may be from 0.5 µm to 10 µm.

The probe beam source 40 is used to generate a probe beam of radiation 41. The light source is typically either a laser or a broadband or white light source for generating a polychromatic probe beam. The probe beam is directed towards the lens 30 by the beam splitter/combiner 42. The probe 41 is focused onto the sample 32 using a lens 30 in a manner so that the rays within the probe beam create a spread of angles of incidence. In the preferred embodiment, the probe beam is directed normal to the surface but can be arranged off-axis as illustrated in U.S. Pat. No. 5,166,752 incorporated by reference. Preferably lens 30 has a high numerical aperture of at least 0.5 to create a spread of angles of incidence from zero to about 30 degrees. In a preferred embodiment, the lens has a numerical aperture of 0.9 to create a spread of angles of incidence from zero to about 70 degrees. The lens 30 is positioned to create a probe beam spot on the sample from 0.5 µm to 10 µm. In the preferred embodiment, the probe beam spot is coincident with the pump beam spot on the sample but can be arranged to be displaced by a certain distance in a sample plane.

The reflected/diffracted probe beam is deflected by the beam splitter/combiner 50 and is measured by a detector array 60. An array of photodetector elements is used to measure the rays within the reflected/diffracted probe beam having a spread of angles of incidence. The detector 60 can also be configured to measure a total intensity of the reflected/ diffracted probe beam by summing the output of the arrays. The sum signal could be used in a manner similar to a conventional MOR system.

As discussed in the above cited patents, an image of the reflected beam as it exists in the plane of lens 30 should be imaged onto the array detector 60. As illustrated in FIG. 1, lens 62 magnifies and relays an image of the sample at the focal plane of lens 30. A spatial filter 64 having an aperture is placed in the focal plane of the lens 62 for controlling the size of the are of the sample which is measured. The imaging optics permit mapping of the radial position of the rays at the lens onto the array so that angle of incidence information can be derived based on the position of the elements in the array. The detector can be a two-dimensional array such as a CCD camera.

Preferably, a color filter 66 is provided in probe beam path to the detector array to block pump beam light from reaching the detector.

As noted above, the output signal from the detector array is passed to a filter 70 for isolating the beam intensity changes that are synchronous with the pump beam modulation. For most implementations, filtering is performed using a heterodyne or lock-in detector (See U.S. Pat. No. 5,978,074 and, in particular, FIG. 2 for a discussion of such a lock-in amplifier/detector).

The signals from filter 70 are sent to processor 72 for analysis. The above-cited patents describe various analysis approaches. In addition to the prior approaches, the additional information that is derived from multiple angle of incidence measurements will open other approaches. For example, additional data points may permit fitting the results to predicted characteristics in a similar manner known to those skilled in the art of multilayer dielectric thin film analysis. (See "Characterization of titanium nitride (TiN) films on various substrates using spectrophotometry, beam profile reflectometry, beam profile ellipsometry and spectroscopic beam profile ellipsometry," Leng, et al., Thin Solid Films, Volume 313 314, 1998, pages 309 to 313, incorporated herein by reference.) In an ellipsometric configuration (beam profile ellipsometry—BPE), additional elements such as polarizers, and/or compensators (waveplates) (as shown generally in phantom at 80 and 82) are used to determine the change in polarization state of the rays within the probe beam induced by the interaction with the sample. See, U.S. Pat. No. 5,042,951, incorporated herein by reference. In the subject method, the change in polarization state of the rays are determined based on a measurement of the modulated changes in reflectivity at multiple angels of incidence. The ellipsometric approach may be implemented with a rotating compensator and a two dimensional detector array as shown in U.S. Pat. No. 7,206,070, incorporated herein by reference.

In general, the subject invention is an improved MOR system. In the prior art MOR system, only intensity (or I and Q) were measured and used to evaluate the sample. In this invention, the lens is used to create a spread of angles of incidence and an array detector is arranged to monitor various rays within the reflected probe beam and mapped to particular angles of incidence. It is believed that variations in the signal as a function of angle of incidence will produce more information.

The assignee herein has developed a large body of technical improvements and variants to the MOR technology. It is believed that the subject simultaneous multiple angle of incidence approach disclosed herein can be extended to many if not all of these prior technical improvements. Since these variants are the subject of prior patent and published applications, only a brief discussion will be set forth herein. In each case, the detector of the prior design would be modified to include a configuration suitable to resolving angle of incidence information. In its most basic form, a one dimensional array detector could be used. Preferably at least two, perpendicular one dimensional arrays would be used. Alternatively, a full, two dimensional detector array could be used. In addition, and as will be discussed below, a quad detector might be used to measure integrated angle of incidence information.

Advanced Applications in Ion Implantation

In the last few years, the assignee herein has developed various approaches to expand the capabilities of the its Therma-Probe device. It is believed that these approaches can be improved by using the extra information that can be obtained with a simultaneous multiple angle of incidence measurement.

For example, U.S. Pat. No. 6,989,899 describes a method of plotting the in-phase and quadrature measurements to simultaneously derive information about ion implantation dose and/or dopant depth profiles. U.S. Pat. No. 7,248,367 teaches how the in-phase and quadrature measurements can be used to measure USJ profile abruptness. U.S. Patent Publication 2006/0166385 describes using in-phase and quadrature measurements to determine peak carrier concentrations in ultra shallow junctions. The patents and patent applications cited herein are incorporated by reference.

As can be appreciated, there are a number of applications related to ion implantation that can be addressed by the subject invention. For the purposes herein the term "dopant characteristics" as used in the claims is intended to broadly cover all of these applications, including, but not limited to extent of damage, damage profile, dopant concentration, dopant profile—both before and after anneal, and wherein the dopant profile includes ultra shallow junction depth, USJ profile, USJ peak carrier concentration, abruptness, etc.

Improved Repeatability

U.S. Patent Publication No. 2005/0195399, incorporated herein by reference, teaches how the repeatability of wafer uniformity measurements can be improved by taking spatially averaged measurements. Additional information can be obtained using the simultaneous multiple angle of incidence measurement approach of the subject invention.

Wavelength Variants

When originally introduced, the assignee's Therma-Probe device used visible light sources at two different wavelengths to create the pump and probe beams. It has been recognized that different wavelengths may be useful in certain circumstances. For example, U.S. Pat. No. 7,126,690 describes the benefits of using a probe beam with a UV wavelength. U.S. Patent Publication No. 2004/0253751 describes the benefits of using a UV pump beam. U.S. Pat. No. 7,106,446 describes the benefits of using multiple wavelengths for either or both the pump and probe beams. U.S. Patent Publication No. 2005/0062971 described the benefits of using a tunable light source for either the pump or the probe beam. In addition, the latter patent also discusses taking measurements at varying spot separations and varying pump beam modulation frequencies. Additional information can be obtained using the a simultaneous multiple angle of incidence measurement approach of the subject invention.

It should be noted that U.S. Pat. No. 5,412,473 includes a discussion of detector configurations which would allow measurement of both angles of incidence and wavelength simultaneously. The patents and patent applications cited herein are incorporated by reference.

Additional examples of spectroscopic reflectometers and ellipsometers suitable for probe beam profile MOR analysis can be found in U.S. Pat. Nos. 5,608,526 and 5,798,837 incorporated herein by reference.

Fourier Lens System

In the system discussed with respect to FIG. 1, lens 62 relays an image of the sample in the focal plane of lens 30 onto the detector. As described in the basic BPR patent (4,999,014), rays having varying angles of incidence map to different radial positions on the detector, with the lowest angles of incidence mapping to the center of the detector and the highest angles of incidence mapping to radially outer locations.

This relationship can be reversed if the optics are arranged to form a Fourier transform of the image. Such an approach is disclosed in U.S. Pat. Nos. 4,870,263 and 5,880,845 both incorporated herein by reference. As seen in FIG. 2 of U.S. Pat. No. 5,880,845, the rays with highest angles of incidence with respect to the sample map to the radially inner portion of the detector while the rays with the shallowest angles of incidence map to the radially outer portion of the detector. For some applications, the Fourier transform mapping approach may be preferred. The scope of the subject invention includes such an approach. A multiple wavelength spectroscopic version of the Fourier transform imaging approach is described in EP 1,640,706, incorporated herein by reference.

Integrated Simultaneous Multiple Angle of Incidence Measurements

In all of the embodiments discussed above, the photodetector included an array arranged so that particular angles of incidence of rays striking the sample could be mapped to radial positions on the detector.

In a variant to this approach, a quad cell detector can be used to determine ellipsometric information using an integrated, simultaneous multiple angle of incidence approach. In this system, as described in U.S. Pat. No. 5,181,080, incorporated herein by reference, the reflected probe beam is passed through a waveplate and a polarizer and directed to a quad cell—see FIG. 2 of the U.S. Pat. No. 5,181,080. Ellipsometric information can be derived by subtracting the sums of the intensity information obtained from orthogonal quadrants. As noted in the U.S. Pat. No. 5,181,080, the resulting signal provides an accurate measurement of the ellipsometric parameter δ for thin films. In this embodiment, the polarizing elements would include a retarder and a polarizer.

In accordance with the subject invention, enhanced detection can be achieved by intensity modulating the sample with a pump beam. To achieve this goal, the lay-out of FIG. 1 herein would be modified to include a waveplate and a polarizer and a quad cell would be used in place of the detector array.

U.S. Pat. No. 6,678,046, incorporated herein by reference, describes how the quad cell arrangement discussed above can be replaced by a eight segment detector as well as a two dimensional array. U.S. Pat. No. 5,596,411, incorporated herein by reference describes how the integrated multiple angle of incidence approach can be used to obtain ellipsometric information at multiple wavelengths simultaneously. In accordance with the subject invention, both of the latter approaches can be improved by periodically exciting the sample with a pump beam.

Applications in Thin Film Metrology

As discussed above, the simultaneous multiple angle of incidence approach (without pump beam modulation) has been used extensively by the assignee in thin film metrology. It may be possible to enhance the thin film measurements using the concepts of the subject invention, which would include adding pump beam modulation and synchronous detection. It should be noted however, that it is currently believed that the largest improvements achieved by the subject invention will relate to dopant measurements as the modulated optical reflectivity signal is known to vary quite significantly in response to different dosage parameters such as concentration, depth, etc.

Recent examples of the use of simultaneous multiple angle of incidence measurements in the field of scatterometry are disclosed in U.S. Pat. Nos. 6,429,943 and 6,813,034, both of which are incorporated herein by reference. It may also be possible to use the subject invention for wafer defect detection and analysis.

While the subject invention has been described with reference to a preferred embodiment, various changes and modifications could be made therein, by one skilled in the art, without varying from the scope and spirit of the subject invention.

We claim:

1. An apparatus for evaluating a sample comprising:
    an intensity modulated energy source for periodically exciting the sample;
    a probe beam of radiation;
    a first optical element for focusing the probe beam onto the sample within a region which has been periodically excited and in a manner so that the rays within the probe beam create a spread of angles of incidence;
    a detector array for monitoring the reflected probe beam;
    a second optical element for relaying an image of the sample from the focal plane of the first optical element to said detector array with said detector array simultaneously generating a plurality of output signals corresponding to the modulated intensity of the probe beam at a plurality of different angles of incidence; and
    a processor for evaluating properties of a sample based on the output signals.

2. An apparatus as recited in claim 1, wherein said intensity modulated energy source is an intensity modulated radiation pump beam.

3. An apparatus as recited in claim 2, wherein said radiation pump beam is generated by a laser.

4. An apparatus as recited in claim 1, wherein the probe beam is generated by a laser.

5. An apparatus as recited in claim 1, wherein said optical element has a numerical aperture of at least 0.5.

6. An apparatus as recited in claim 1, wherein said optical element has a numerical aperture of about 0.9.

7. An apparatus as recited in claim 1, further including polarizing elements configured so that the processor can determine the change in polarization state of rays within the reflected probe beam at a plurality of angles of incidence.

8. An apparatus for evaluating a semiconductor sample comprising:
    an intensity modulated pump beam of radiation which is directed to the sample in a manner to periodically excite the sample and generate thermal and plasma waves which effect the reflectivity at the sample surface;
    a probe beam of radiation;
    a first optical element for focusing the probe beam onto the sample within a region which has been periodically excited and in a manner so that the rays within the probe beam create a spread of angles of incidence;
    a detector array for monitoring the reflected probe beam;
    a second optical element for relaying an image of the sample from the focal plane of the first optical element to said detector array with said detector array simultaneously generating a plurality of output signals corresponding to the modulated intensity of the probe beam at a plurality of different angles of incidence; and a filter for processing the output signals to isolate the changes in reflectivity synchronous with the pump beam modulation frequency with the results being used to evaluate the sample.

9. An apparatus as recited in claim 8, wherein the filter generates separate in-phase and quadrature outputs.

10. An apparatus as recited in claim 9, further including a processor which determines the amplitude of the modulated intensity of the probe beam at a plurality of angles of incidence based on the in-phase and quadrature outputs.

11. An apparatus as recited in claim 9, further including a processor which determines the dopant characteristics within the semiconductor sample based on the in-phase and quadrature outputs.

12. An apparatus as recited in claim 8, wherein said optical element has a numerical aperture of at least 0.5.

13. An apparatus as recited in claim 8, wherein the probe beam is generated by a laser.

14. An apparatus for evaluating a sample comprising:

an intensity modulated energy source for periodically exciting the sample;

a probe beam of radiation;

a first optical element for focusing the probe beam onto the sample within a region which has been periodically excited and in a manner so that the rays within the probe beam create a spread of angles of incidence;

a retarder;

a polarizer;

a detector for monitoring the reflected probe beam light along two orthogonal axes after the probe beam has passed through the retarder and the polarizer;

a second optical element for relaying an image of the sample from the focal plane of the first optical element to said detector with said detector generating output signals that integrates the modulated intensity of the various rays having different angles of incidence, said output having two components corresponding to said two orthogonal axes; and a processor for evaluating properties of a sample based on the output signals.

15. An apparatus as recited in claim 14, wherein said intensity modulated energy source is an intensity modulated radiation pump beam.

16. An apparatus as recited in claim 14, wherein said optical element has a numerical aperture of at least 0.5.

17. A method apparatus for evaluating a semiconductor sample comprising the steps of:

periodically exciting the sample in a manner to generate thermal and plasma waves which effect the reflectivity at the sample surface;

focusing a probe beam of radiation onto the sample within a region which has been periodically excited using a first optical element and in a manner so that the rays within the probe beam create a spread of angles of incidence;

relaying an image of the sample from the focal plane of the first optical element to a detector array for monitoring the reflected probe beam and generating a plurality of output signals corresponding to the modulated intensity of the probe beam at a plurality of different angles of incidence;

filtering the output signals to isolate the changes in reflectivity synchronous with the periodic excitation frequency with the results being used to evaluate the sample; and storing the results of the evaluation.

18. A method as recited in claim 17, wherein the step of periodically exciting the sample is performed by directing an intensity modulated pump beam to the surface of the sample.

19. A method as recited in claim 17, wherein the step of periodically exciting the sample is performed by dithering the position of a pump beam on the surface of the sample.

20. A method as recited in claim 17, wherein the filtering step generates separate in-phase and quadrature outputs.

21. A method as recited in claim 20, further including the step of determining the amplitude of the modulated intensity of the probe beam at a plurality of angles of incidence based on the in-phase and quadrature outputs.

22. A method as recited in claim 20, further including the step of determining the dopant characteristics within the semiconductor sample based on the in-phase and quadrature outputs.

23. A method as recited in claim 17, wherein the probe beam is focused onto the sample to create a spread of angles of incidence of at least thirty degrees.

24. A method as recited in claim 17, further including the step of determining the change in polarization state of rays within the reflected probe beam at a plurality of angles of incidence.

* * * * *